(12) United States Patent
Wornson et al.

(10) Patent No.: US 7,710,558 B2
(45) Date of Patent: May 4, 2010

(54) AUTOMATED ONLINE MEASUREMENT OF GLASS PART GEOMETRY

(75) Inventors: Douglas Wornson, Northfield, MN (US); Eric L. Hegstrom, Tucson, AZ (US); Mark M Abbott, Dundas, MN (US)

(73) Assignee: LiteSentry Corporation, Dundas, MN (US)

( * ) Notice: Subject to any disclaimer, the term of this patent is extended or adjusted under 35 U.S.C. 154(b) by 0 days.

(21) Appl. No.: 12/208,415

(22) Filed: Sep. 11, 2008

(65) Prior Publication Data

US 2010/0060902 A1    Mar. 11, 2010

(51) Int. Cl.
*G01N 21/00* (2006.01)
(52) U.S. Cl. ................... 356/239.1; 356/239.7
(58) Field of Classification Search ... 356/239.1–239.4, 356/237.1–237.5
See application file for complete search history.

(56) References Cited

U.S. PATENT DOCUMENTS

| | | | | |
|---|---|---|---|---|
| 5,343,288 A * | 8/1994 | Cohen et al. | ............. | 356/239.1 |
| 5,642,198 A * | 6/1997 | Long | ........................... | 356/430 |
| 5,680,217 A * | 10/1997 | Yli-Vakkuri | ................. | 356/602 |
| 7,385,710 B1 * | 6/2008 | Sturgill | ....................... | 356/632 |
| 7,532,333 B2 * | 5/2009 | Haeusler et al. | ............. | 356/612 |
| 7,551,274 B1 * | 6/2009 | Wornson et al. | ......... | 356/239.1 |
| 2005/0018199 A1 * | 1/2005 | LeBlanc | ...................... | 356/477 |
| 2007/0296963 A1 * | 12/2007 | Parker et al. | ............. | 356/240.1 |
| 2008/0316501 A1 * | 12/2008 | Hirata et al. | ................. | 356/601 |

* cited by examiner

*Primary Examiner*—Michael P Stafira
(74) *Attorney, Agent, or Firm*—Edward Weck

(57) ABSTRACT

An apparatus which measures a size and a shape of a transparent sheet includes a conveyor, a lighting apparatus, an imaging device and a process controller. The conveyor moves the transparent sheet. The lighting apparatus projects light onto the transparent sheet. The imaging device receives reflected light reflected from the transparent sheet. A thickness is input into the process controller. A sheet temperature from a sheet temperature sensor and/or a structure temperature from a structure temperature sensor are output to the process controller. An image is output from the imaging device to the process controller. The process controller outputs the size and the shape of the transparent sheet. The outputs from the process controller are used to adjust machine tools used to fabricate the transparent sheet.

24 Claims, 8 Drawing Sheets

AUTOMATED ONLINE MEASUREMENT OF GLASS PART GEOMETRY

BACKGROUND OF THE INVENTION

1. Summary of the Invention

The present invention relates to an automated measurement system and methods for measuring the size and shape of glass sheets.

2. Description of the Related Art

In processes for manufacture of glass in sheet form, it is necessary to be able to inspect the sheets of glass for defects. It is important to be able to conduct the inspection on-line in the manufacture process, at production speeds, so that defects may be rapidly identified, this information communicated with production personnel and the glass sheets with defects may readily be separated in an effective manner from glass sheets meeting quality specifications.

During the production of glass sheets, it is important that the glass sheet produced be of a precise size and shape. Glass sheets are currently produced in a variety of specified sizes and shapes. Current inspection of glass sheets for various geometries, including size and shape, in the glass production industry is semi-automated and involves mechanical fixtures or dyes, limited caliper measurements and sampling a subset of production for inspection. Pencil probes can also be used to directly mechanically measure the size and shape of an individual glass sheet. Current inspection systems for glass sheets of various geometries often rely on human measurement and human intervention with the production line to alter upstream parameters of a glass production system. Such manual processes introduce a large amount of variability in the outgoing inspection product. Until recent advances in large area sensors, attempts at precision, non-contact measurements of large area glass sheets using machine vision required multiple sensors. However, the use of multiple sensors imposes problems of camera to camera registration and the inherent loss of accuracy.

A need exists for an automated inspection system which determines the size and shape of a glass sheet.

SUMMARY OF THE INVENTION

Apparatus and methods in accordance with the present inventions may resolve many of the needs and shortcomings discussed above and will provide additional improvements and advantages as will be recognized by those skilled in the art upon review of the present disclosure.

The geometric measurement apparatus of this invention measures the size and the shape of a transparent sheet. The geometric measurement apparatus according to this invention may be used to inspect optically transparent sheets of various kinds including glass, coated glass, mirrored glass, acrylic, polycarbonate, and other optically transparent or transmissive polymer sheets. Other optically transparent or optically transmissive (high transmission) polymer sheets include, and are not limited to, polypropylene and polyethylene. The geometric measurement apparatus of the present invention may be used to inspect translucent or opaque sheets.

A glass sheet cut for a particular end-use may be of a complicated shape and with the shape having holes and cutouts (or voids) therein. The method and apparatus of the present invention can confirm the exact location and geometry of the holes and cutouts and the particular shape of the glass sheet. In addition, the glass sheet may have a marginal edge which is beveled and which may be variable with respect to such features such as the angle of bevel, surface quality, uniformity of bevel and the like. The beveled edge may be a rounded or edge treatment of the glass other than a 90 degree edge. Beveled glass sheets are described in U.S. Pat. No. 4,397,118 which is hereby incorporated by reference. The method and apparatus of the present invention can confirm the surface quality of the bevel, the uniformity of bevel and the like. The position of the glass sheet within the apparatus is not important, as the entire conveyor is illuminated and the field of view of the camera encompasses the full width of the conveyor. In addition, the present invention may be used with curved glass.

The geometric measurement apparatus according to this invention may analyze glass while being moved on a conveyor in a production process. The glass moving on the conveyor may be of the various sizes and shapes used in commercial glass production. The conveyor for moving glass may be oriented vertically, nearly vertically or horizontally. The conveyor may employ a belt or rollers or donuts for moving the transparent sheets. The conveyor may employ an air float system to move the transparent sheets. The conveyor may be operable at a velocity up to 2 m/sec or higher. The conveyor may transport glass of widths up to 3.5 m, and from 0.1 mm to 25 mm in thickness. The geometric measurement apparatus according to this invention may analyze glass which is not being moved or is stationary on the conveyor in the production process. These static measurements may be with a simple table or a complex robot holding the glass.

The geometric measurement apparatus in accordance with the present invention may provide a retroreflective photoeye for tracking a position of a glass sheet along the conveyor. The retroreflective photoeye may be positioned at the pass line of the glass sheet on the conveyor. The retroreflective photoeye transmits information about the position of the transparent sheet on the conveyor to an imaging device or camera. The retroreflective photoeye may trigger the lighting apparatus to be illuminated and may trigger the imaging device to take an image at a precise time related to the precise position of the glass sheet on the conveyor. Other means of triggering the lighting apparatus and the imaging device by tracking the position of a glass sheet along a conveyor may be used with the geometric measurement apparatus including throughbeam photoeyes, mechanical limit switches, light curtain limit switches, proximity switches or tracking of the parts using motion control equipment such as servo drive controllers.

The geometric measurement apparatus in accordance with the present invention provides an imaging device or camera for capturing an image of the glass sheet. The present invention may be used with one or a plurality of cameras. The camera or cameras may be located on either side of the glass sheet. The camera used may be an area scan CCD camera like the one manufactured by Lumenera Corporation. Cameras used may be up to 50 megapixels. Area scan CMOS cameras or line scan cameras may be used with the geometric measurement apparatus. Light curtains, linear CCD arrays, one-dimensional arrays of photoreceptors or two-dimensional arrays of photoreceptors may be used with the present invention.

The geometric measurement apparatus in accordance with the present invention provides a lighting apparatus. The lighting apparatus may be on the same side of the glass as the camera or the glass sheet may intervene between the lighting apparatus and the camera. The lighting apparatus may include a number of LED lights parallel to the direction of glass flow along the conveyor and at a high angle of incidence to the glass sheet. The LED lights may extend for up to 8 meters along the conveyor. The wavelength of the LED lights is selected to optimally match the wavelength sensitivity of the camera. Other lights may be used with the geometric measurement apparatus including alternative wavelength LED lights, UV lights, IR lights, strobe lights, fluorescent lights, halogen lights, incandescent lights, and laser projections including lines, grids and moiré patterns or other light generally known to one skilled in the art.

The geometric measurement apparatus in accordance with the present invention may provide a structure temperature sensor and/or a sheet temperature sensor. The structure temperature sensor, if present, sends a structure temperature signal to the process controller. The sheet temperature sensor, if present, sends a sheet temperature signal to the process controller. The signal from the structure temperature sensor and/or the signal from the sheet temperature sensor allow the geometric measurement apparatus to adjust the size and shape of the glass sheet measured in accordance with thermal expansion calculated. As the temperature of the glass sheet increases, the size and shape of the glass sheet increases. As the ambient temperature increases, the structural materials comprising the structure of the geometric measurement apparatus thermally expand requiring compensating adjustments to the size and shape of the glass sheet. The structure temperature sensor may include transistor thermocouples, like the EI1022 temperature probe manufactured by Electronics Innovations Corp. (Lakewood, Colo.). The sheet temperature sensor may include non-contact infrared temperature detectors with thermocouple, voltage or current output like the O565 sensor manufactured by Omega Engineering, Inc. (Stamford, Conn.). Other temperature sensors known in the art may also be used with the present invention The geometric measurement apparatus in accordance with the present invention may provide a thickness sensor. The thickness sensor measures the thickness of the glass and transmits a thickness signal to the process controller. The geometric measurement apparatus may require compensating adjustments to the apparent size and apparent shape of the glass sheet depending on the thickness of the glass sheet. Thickness sensors may include the Version 5 triangulating laser thickness sensor manufactured by LiteSentry Corporation (Dundas, Minn.). Other thickness sensors known in the art may also be used with the present invention The geometric measurement apparatus in accordance with the present invention may provide a process controller. The process controller may receive an input signal from the camera, the retroreflective photoeye, the lighting apparatus, the structure temperature sensor, the sheet temperature sensor, and the thickness sensor. The process controller may send an output signal to control a machine tool or a pass/fail signal to accept or reject a glass sheet. Glass machine tools include tools for cutting, grinding and drilling. The drilling and grinding equipment may be like the diamond wheel linear X-Y grinder and other grinders and drills manufactured by Glassline Corporation (Perrysburg, Ohio) and robotic grinders with a wheel grinder manufactured by HEGLA GmbH & Co. KG (Beverungen, Germany). The process controller may send output signals to other process devices upstream or downstream from the geometric measurement apparatus.

The geometric measurement apparatus in accordance with the present invention may provide a user interface. The user interface may provide a pass/fail indication in rejecting a glass sheet, historical trend graphs of the size and shape of glass sheets, detailed images of the sheet showing specific points of failure and the ability to record and review images of parts historically measured as well as other features of utility to the user.

A calibration target may be used with the present invention to calibrate, or standardize, the geometric measurement apparatus by determining a deviation from a standard so as to correlate optical image dimensions to physical dimensions. The calibration target may have one of a variety of two-dimensional patterns. The calibration target may be a chessboard comprising a plurality of squares, of black and white which are high contrast. The calibration target may be etched on glass or the target may be laser-cut from a sheet of plastic material. The calibration target pattern may be comprised of annular concentric circular lines, a regular array of circles with a central void or radial lines passing through a central point and equidistant from one another, like the spokes of a wheel. Other regular patterns may be used for the calibration target. The calibration target or a combination of multiple calibration targets should have a greater area or a greater size than the glass sheet to be measured.

Inspection of glass sheets that have passed through a cutting, grinding and drilling production process may indicate a number of defects. The defects in the glass sheets may be a direct result of specific settings on the glass machine tools. An inspection station located downstream from the glass machine tools measures inspection parameters of glass sheets passing through the inspection station. The glass machine tools may be adjusted with the input derived from the results obtained from inspection of glass sheets passing the inspection station. Inspection parameters that may be inputs for the closed loop control of a glass machine tool process include length of the glass sheet, width of the glass sheet, diameter and position of holes in the glass sheet, position and shape of cutouts in the glass sheet, diagonal lines across the glass sheet, angle and size of corner dubbing of the glass sheet, and the thickness of the glass sheet.

Specific inspection parameter outputs from the geometric measurement apparatus may include but are not limited to; (1) the length of the glass sheet, (2) the width of the glass sheet; (3) the position of holes on the glass sheet; (4) the position of cutouts on the glass sheet; (5) the length of diagonal lines across the glass sheet; (6) the angle and size of corner dubbing on the glass sheet; and (7) the thickness of the glass sheet. The size of the glass sheet includes (1) and (2), above, and the shape of the glass sheet includes (3) through (7), above. Further, statistics may be derived from the above inspection parameters including average, mean, 1, 2, 3 or more standard deviations from a norm, histograms and distributions of data, and trends of said data over time. Further, area statistics may be derived to judge particular areas of the glass sheets relative to other areas of the glass sheets. Multiple quality thresholds for any of the inspection parameters may be used to judge the quality of the glass sheets and report departure from the target quality, even if the quality of the glass sheet does not represent a "failure". In this manner inspection parameters of a wide range and variety may be sent to the geometric measurement apparatus, providing information from which to make changes to the glass machine tool settings. Adjustments to the glass machine tools may make the glass sheet longer or shorter, wider or narrower, holes with a larger or smaller diameter, cutouts with a larger or smaller size, or corner dubbing of different geometries.

The present invention is more economical and results in fewer discarded pieces of unusable glass. The geometric measurement apparatus measures the size and shape with an accuracy of the measurement to a tolerance of less than +/−0.5 mm. Existing manual inspection techniques are less accurate and result in significant production of glass sheets prior to discovery of defects, thereby resulting in potentially large volumes of defective glass sheets being produced.

The present invention solves the problems, among others, of lens distortion, parallax, image blur and thermal expansion of both the glass sheets and the structure comprising the geometric measurement apparatus. In the absence of correction, lens distortion of the camera causes the image of the glass sheet to appear curved on all edges (keystoning or barrel distortion). In the absence of correction, the parallax between the camera and the glass sheet causes the glass sheet to appear larger than it actually is because the rays of light entering the camera are not transverse to the direction of movement at the edges of the glass sheet. In the absence of correction, movement of the glass sheet causes the image of the glass sheet to blur or appear fuzzy on the leading edge and the trailing edge. In the absence of correction, thermal expansion or contraction of the glass sheet causes a change in the apparent size of the glass sheet. In the absence of correction, thermal expansion or contraction of the structure comprising the geometric measurement apparatus causes a change in the apparent size of the glass sheet. The present invention provides corrections for lens distortion, parallax, image blur and thermal expansion of both the glass sheets and the structure comprising the geometric measurement apparatus to alleviate these problems.

The present invention also solves the problem of measurement of bow, or warp, on a glass sheet. The non-uniform heating of the glass sheet, either through the heat treatment process or through deposition processes may result in non-uniform change in the geometry of the glass sheet. Such non-uniform changes in the geometry may be termed bow. Bow, or warp, is the curvature of the glass sheet over the entire length and width of the glass sheet or over local areas of the glass sheet. Bow of the transparent sheet is measured by projecting a fixed pattern, such as a grid of lines, superimposed over the conveyor area. The change in size and shape of the reflected fixed pattern image is measured and this information is used to compute the bow intensity at locations over the surface of the flat sheet Other features and advantages of the invention will become apparent from the following detailed description, and from the claims.

BRIEF DESCRIPTION OF THE DRAWINGS

All Figures are illustrated for ease of explanation of the basic teachings of the present invention only; the extensions of the Figures with respect to number, position, relationship and dimensions of the parts to form the preferred embodiment will be explained or will be within the skill of the art after the following description has been read and understood. Further, the exact dimensions and dimensional proportions to conform to specific force, weight, strength, and similar requirements will likewise be within the skill of the art after the following description has been read and understood.

DETAILED DESCRIPTION OF THE INVENTION

The figures generally illustrate exemplary embodiments of a geometric measurement apparatus 10 or components thereof which include aspects of the present inventions. The particular embodiments of the geometric measurement apparatus 10 illustrated in the figures have been chosen for ease of explanation and understanding of various aspects of the present inventions. These illustrated embodiments are not meant to limit the scope of coverage but instead to assist in understanding the context of the language used in this specification and the appended claims.

The present invention provides a geometric measurement apparatus 10 and methods for implementing the geometric measurement apparatus 10. In certain aspects, the geometric measurement apparatus 10 in accordance with the present inventions may be used to measure a size and a two dimensional shape of a glass sheet 12. The geometric measurement apparatus 10 may also be used to detect defects in a bevel of a marginal edge of a glass sheet 12, including edge grind quality, the inside diameter of the beveled edge and the outside diameter of the beveled edge.

Figure 6A:
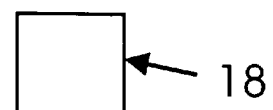
FIGS. 6A, 6B and 6C of the drawings show cross sectional stylized views of a glass sheet exhibiting warp or bow.
Figure 6A:
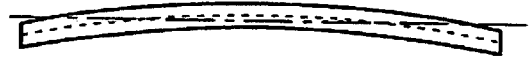
Figure 7A:
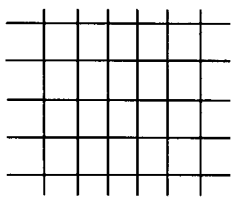
FIGS. 7A, 7B and 7C of the drawings show a top view of a fixed pattern reflected from a glass sheet exhibiting warp or bow.
Figure 6B:
Figure 7B:
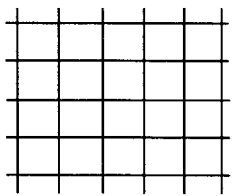
Figure 6C:
Figure 7C:
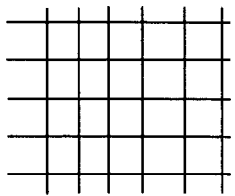

The geometric measurement apparatus 10 may also be used to detect bowing of a glass sheet 12, as shown in FIGS. 6A, 6B and 6C. A regular grid of lines, or fixed pattern, is projected onto the length and width of the glass sheet 12. A reflected image of the fixed pattern is captured by the camera 18. The process controller 28 may compare the reflected image of the fixed pattern with a stored image of the fixed pattern. The change in size and shape of the reflected fixed pattern image is measured and this information is used to compute the bow intensity at locations over the surface of the flat sheet 12. Examples of reflected images of the fixed pattern are shown in FIGS. 7A, 7B and 7C.

A glass sheet 12 has a thickness, a size and a two dimensional shape. The size of the glass sheet 12 derives from measurements of a length and a width of the glass sheet 12. The two-dimensional shape of the glass sheet 12 is not limited to but may include square, rectangular, circular, irregular rectangular, irregular square, and irregular circular shapes. The two-dimensional shape of the glass sheet 12 may have holes 57 drilled in the glass sheet 12. The two-dimensional shape of the glass sheet 12 may have cutouts 59 or voids which are cutout of an edge of the glass sheet 12. The shape of the glass sheet 12 is not limited to but may be quadrilateral, elliptical, irregular, curved, quadrilateral with a quadrilateral removed, quadrilateral with an ellipse removed, elliptical with a quadrilateral removed, elliptical with an ellipse removed, irregular with a quadrilateral removed, irregular with an ellipse removed, curved with a quadrilateral removed, or curved with a quadrilateral removed.

Figure 5:
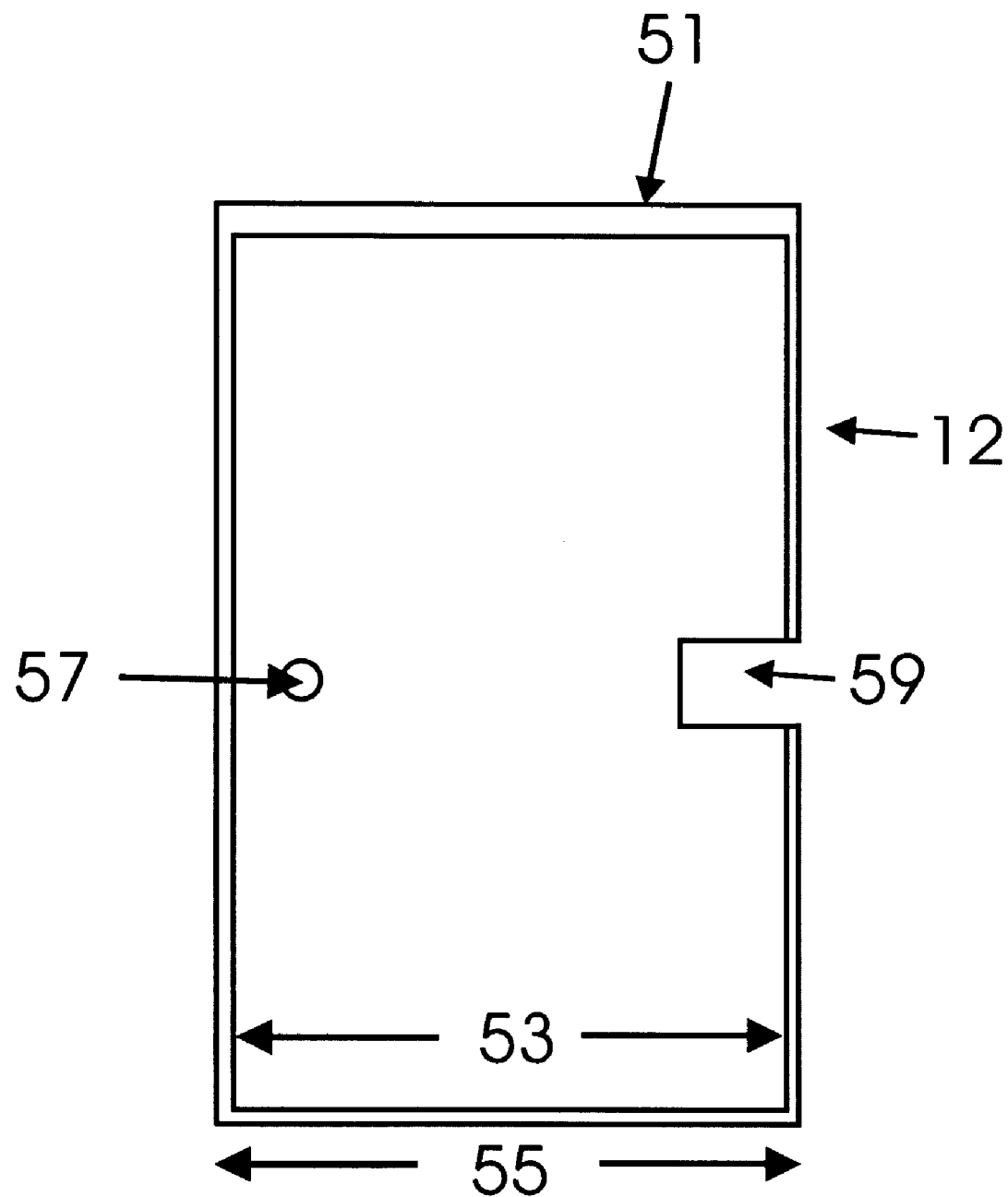
FIG. 5 of the drawings shows size and shape of a glass sheet.

An example of a glass sheet 12 is shown in FIG. 5. The glass sheet 12 may have a marginal edge 51 which is beveled. The glass sheet 12 defines an inside diameter 53 and an outside diameter 55, the space between being defined as the edge treatment resulting from grinding or beveling of the glass sheet 12. The beveled edge of glass sheet 12 is a rounded or flat edge treatment of the glass sheet 12 other than a 90 degree edge. The glass sheet 12 may have a hole 57 and a cutout 59. The geometric measurement apparatus 10 detects defects in the marginal edge 51 of the glass sheet 12 as well as deviations of the inside diameter 53 and the outside diameter 55 from standard values. The geometric measurement apparatus 10 also detects deviations in the diameter and position of the hole 57 and the extent and contour of the cutout 59.

Figure 1A:
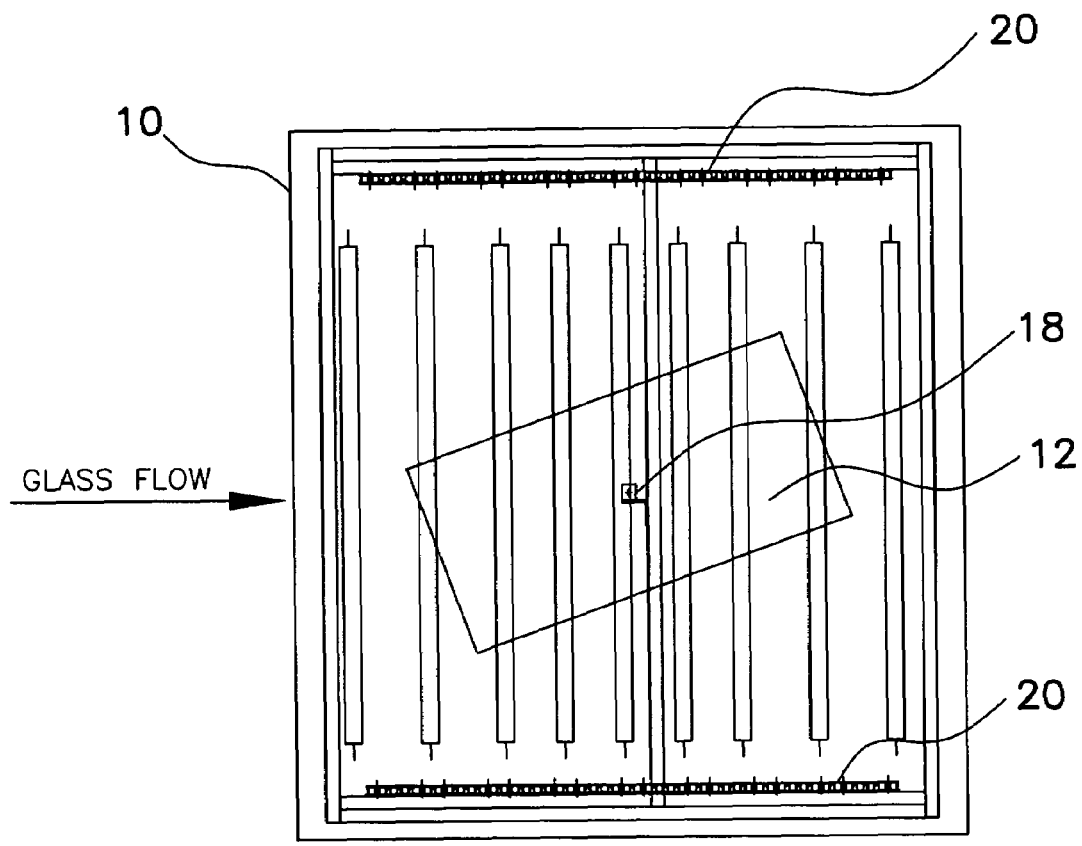
FIG. 1A of the drawings shows a top view of the geometric measurement apparatus.
Figure 1B:
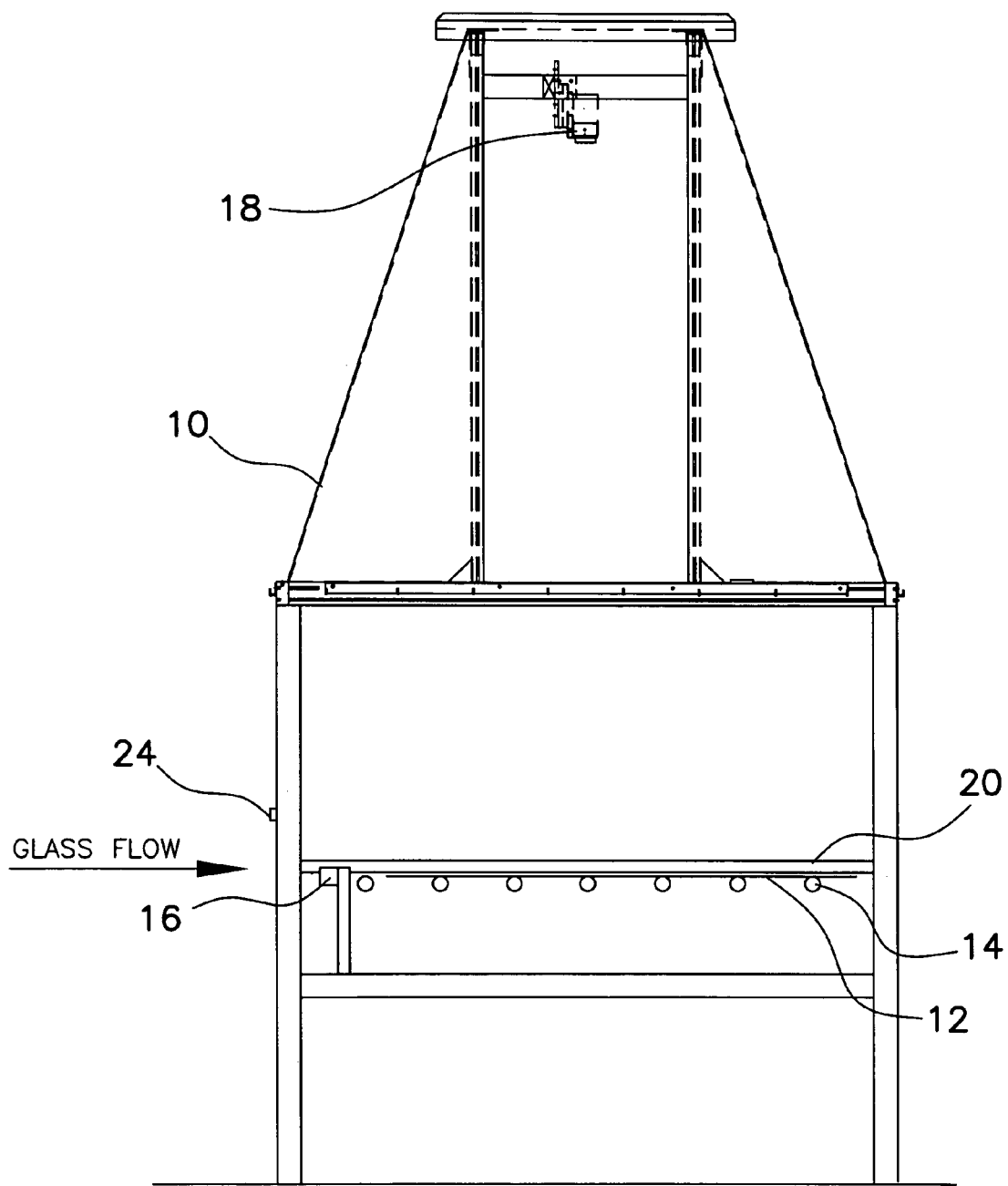
FIG. 1B of the drawings shows a first side view the geometric measurement apparatus system parallel to the glass travel.
Figure 1C:
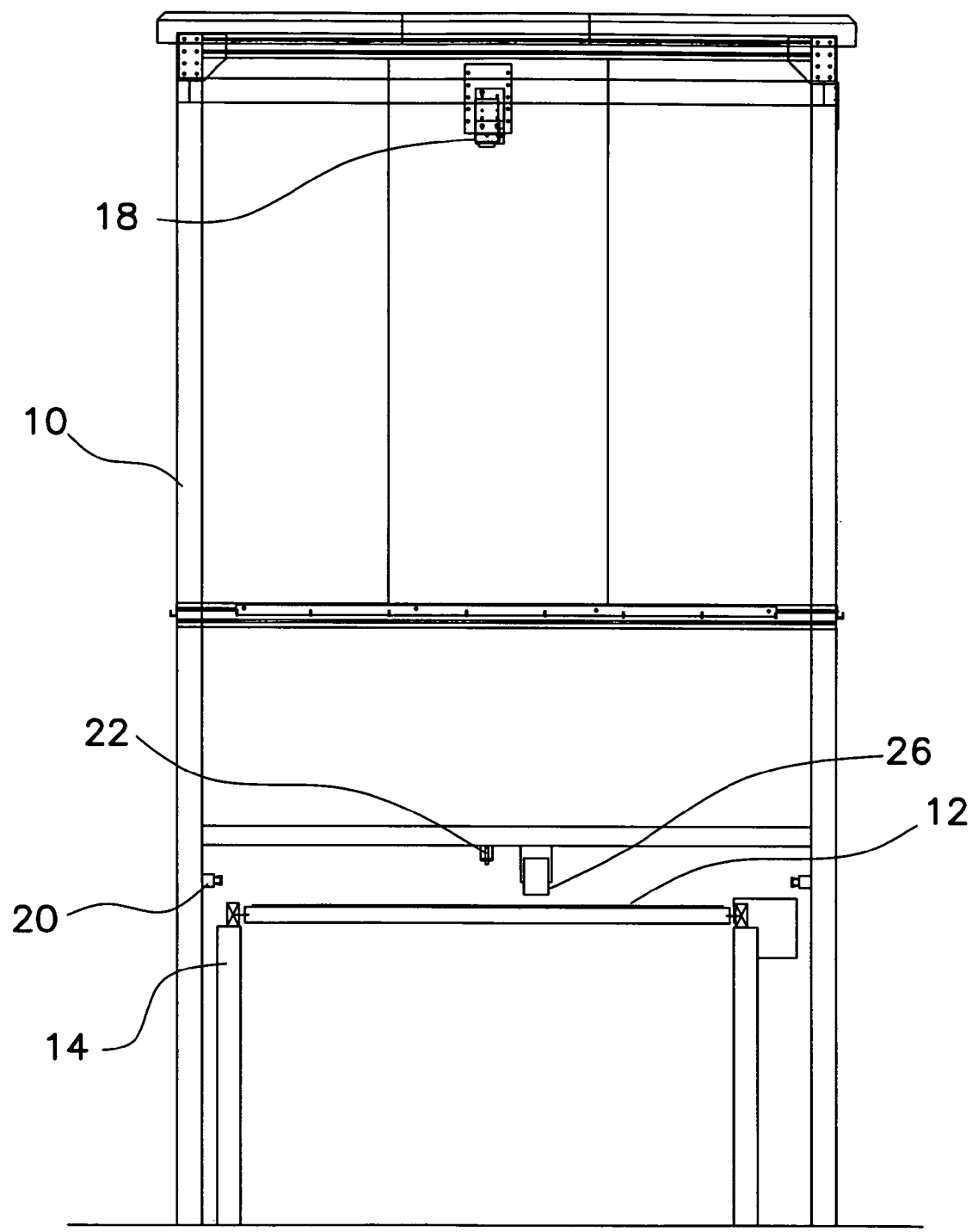
FIG. 1C of the drawings shows a second side view of the geometric measurement apparatus perpendicular to the glass travel.

The geometric measurement apparatus 10 generally comprises a conveyor 14, a retroreflective photoeye 16, a camera 18, a lighting apparatus 20, a sheet temperature sensor 22 for the glass sheet 12, a structure temperature sensor 24, a thickness sensor 26 and a process controller 28. The conveyor 14 transports the glass sheet 12 in the direction of glass flow from left to right as seen in FIGS. 1A and 1B. The glass sheet 12 passes by the thickness sensor 26 and the sheet temperature sensor 22, and then passes by the retroreflective photoeye 16. The lighting apparatus 20 is downstream of, or coincident with, the retroreflective photoeye 16, the sheet temperature sensor 22 for the glass sheet 12 and the thickness sensor 26. As shown in FIGS. 1B and 1C, the camera 18 is located above the glass sheet 12. As shown in FIG. 1A the camera 18 has a field of view that extends from a first side of the conveyor 14 to a second side of the conveyor 14. The field of view of the camera 18 captures an image of the glass sheet when the glass sheet is less than 50 m$^2$.

The retroreflective photoeye 16 such as manufactured by Banner Industries (Danvers, Mass.) used with the geometric measurement apparatus 10 projects a beam of light across the pass line for the glass sheet 12 along the conveyor 14. As a glass sheet 12 travels along the conveyor 14, the leading edge of the glass sheet 12 reflects the light beam across the pass line, and a signal is sent to the process controller 28. When the trailing edge of the glass sheet 12 passes the retroreflective photoeye 16, the light beam is no longer reflected and another signal is sent to the process controller 28.

The imaging device of the geometric measurement apparatus 10 is most generally a camera 18. The camera 18 used is an 11 megapixel (4000×2672 pixel) area scan CCD camera like the one manufactured by Lumenera Corporation. Cameras used may be up to 50 megapixels. Cameras used may be area scan CMOS or Line Scan cameras. The field of view of the camera 18 captures an image with an area of less than 50 m$^2$ at the pass line of the conveyor 14.

The lighting apparatus 20 of the geometric measurement apparatus 10 comprises LEDs like the ones manufactured by Philips Lumileds Lighting Company. The lighting apparatus is located just above the pass line of the glass sheet 12 along the conveyor 14 and directed generally parallel to the glass sheet 12. The lighting apparatus 20 may be directed at a high angle of incidence to the glass sheet 12, with the normal plane to the glass being 0 degrees. The lighting apparatus 20 may be projected at about 9 degrees above the parallel to the glass sheet 12. The lighting apparatus 20 is located generally parallel to the direction of glass flow along the conveyor 14 and external to the rollers of the conveyor 14, but of sufficient length greater than the length of the glass sheet 12 to illuminate the leading and trailing edges of the glass sheet 12. The lighting apparatus 20 comprises a first string of LEDs on a first side of the conveyor 14 and a second string of LEDs on a second side of the conveyor 14. The lighting apparatus 20 may be continuously illuminated or the lighting apparatus 20 may be illuminated in a pulse in response to a signal from the process controller 28 for less than 100 milliseconds.

The geometric measurement apparatus 10 may include a structure temperature sensor 24 and/or a sheet temperature sensor 22. The structure temperature sensor 24 of the geometric measurement apparatus 10 is a temperature sensor like the EI1022 temperature probe manufactured by Electronics Innovations Corp. (Lakewood, Colo.). The structure temperature of a production line can be in the range between 10° C. to 50° C. The structure temperature sensor 24 sends a signal to the process controller 28 indicating the structure temperature of the structure of the geometric measurement apparatus 10.

The sheet temperature sensor 22 of the geometric measurement apparatus 10 is an infrared temperature sensor like those manufactured by Omega Engineering, Inc. (Stamford, Conn.). The temperature of the glass sheet 12 arriving at the sheet temperature sensor 22, although projected to be 20° C., or ambient temperature, can be in the range between 10° C. to 600° C. The geometric measurement apparatus 10 is often positioned immediately following a glass heat treatment process. The sheet temperature sensor 22 measures the thermal expansion of the glass sheet 12 at temperatures above 20° C. The sheet temperature sensor 22 outputs a signal to the process controller 28 of the temperature of the glass sheet 12. The process controller 28 then determines the thermal expansion of the glass sheet 12 based on the signal output from the sheet temperature sensor 22 and the coefficient of thermal expansion for the material comprising the glass sheet 12. The computed thermal expansion of material comprising the glass sheet 12 is used to compute the size and shape of the glass sheet 12 at a standard temperature (20° C., for example).

The thickness sensor 26 of the geometric measurement apparatus 10 measures the thickness of the glass sheet 12. Thickness sensors 26 are like those manufactured by Lite-Sentry Corporation (Dundas, Minn.), Keyence Corporation (Osaka, Japan) or EDTM, Inc. (Toledo, Ohio). The thickness sensor 26 outputs the thickness of the glass sheet 12 to the process controller 28. The thickness may be used to correct the size and shape of the glass sheet 12 for parallax. The thickness may also be used to judge the quality of the glass sheet 12 and to provide a pass/fail signal to accept or reject the glass sheets 12 according to an allowable thickness range.

The process controller 28 receives and sends a variety of input signals and output signals 29 including a photoeye signal from the retroreflective photoeye 16, a sheet temperature signal from the sheet temperature sensor 22, a structure temperature signal from the structure temperature sensor 24, and a thickness signal from the thickness sensor 26. The process controller 28 may send a lighting signal to the lighting apparatus 20 to illuminate the lights for less than 100 milliseconds. After the process controller 28 receives the photoeye signal from the retroreflective photoeye 16, the process controller 28 sends a signal to the camera 18 to capture an image of the glass sheet 12. The process controller 28 compares an image of the glass sheet 12 with a stored value for a standard glass sheet. If the comparison shows that the glass sheet 12 is out of tolerance with the stored value and/or bow intensity of the reflected fixed pattern for the glass sheet standard, the process controller 28 may send a signal to control a glass machine tool 33, and/or a pass/fail signal to accept or reject 35 the glass sheet 12. The conveyor 14 moves the glass sheet 12 at a constant velocity and the process controller 28 corrects the size, length or width of the glass sheet 12 to compensate for the image blur due to the motion of the glass sheet 12.

A calibration target 30 is used to calibrate the geometric measurement apparatus 10. The calibration target 30 may be one of a variety of two-dimensional patterns. The calibration target 30 may be a chessboard with a first side of 1200 mm, a second side of 2000 mm and comprising a plurality of squares, 50 mm on a side, of black and white and of high contrast. The squares have a deviation of less than 0.1 mm on a side. The calibration target 30 may be etched on glass or the calibration target 30 may be laser-cut from a sheet of plastic material. The pattern of the calibration target 30 may be comprised of annular concentric circles, a regular array of circles without a center or radial lines passing through a central point and equidistant from one another, like the spokes of a wheel. The calibration target 30 may also be made with other regular patterns.

The geometric measurement apparatus 10 allows the closed loop control of glass machine tools 33. The geometric measurement apparatus 10 receives inputs from the sheet temperature sensor 22, the structure temperature sensor 24, the thickness sensor 26 and allows the feedback control of glass machine tools 33. Glass sheets 12 that have passed through a cutting, grinding and drilling production process implemented by glass machine tools 33 may have a number of defects. The defects in the glass sheets 12 may be a direct result of specific settings on the glass machine tools 33. The glass machine tools 33 may be adjusted with the input obtained from inspection of glass sheets 12 passing the inspection station. Inspection parameters that may be inputs for the closed loop control of process using glass machine tools 33 may include length of the glass sheet 12, width of the glass sheet 12, diameter and position of holes 57 on the glass sheet 12, extent and contour of cutouts 59 on the glass sheet 12, diagonal lines across the glass sheet 12, the angle and size of corner dubbing geometry of the glass sheet 12, and the thickness of the glass sheet 12.

In this manner, inspection parameters of a wide range and variety may be sent to the geometric measurement apparatus 10, providing information from which to make changes to the settings of the glass machine tools 33. Adjustments to the glass machine tools 33 may result in glass sheets 12 which are longer or shorter, glass sheets 12 which are wider or narrower, holes 57 with a larger or smaller diameter, and/or cutouts 59 with a larger or smaller size.

A method which measures a size and a shape of a glass sheet 12 comprises: projecting light onto the glass sheet 12 from the lighting apparatus 20; receiving the reflected light from the glass sheet 12 with the imaging device or camera 18; outputting an image from the imaging device 18 to the process controller 28; and outputting the size and the shape of the glass sheet 12 from the process controller 28. The method may also include using a calibration target 30 wherein the calibration target 30 has a two dimensional pattern. The method may also include measuring a temperature of the glass sheet 12 with a sheet temperature sensor 22, outputting the sheet temperature of the glass sheet 12 from the sheet temperature sensor 22 to the process controller 28 and using the glass temperature in the process controller 28 to adjust the size and shape of the glass sheet 12. The method may also include measuring a temperature of the structure of the geometric measurement apparatus with a structure temperature sensor 24, outputting the temperature of the structure from the structure temperature sensor 24 to the process controller 28 and using the structure temperature in the process controller 28 to adjust the size and shape of the glass sheet 12. The method may include measuring the temperature of the glass sheet 12 with the sheet temperature sensor 22 and/or measuring the temperature of the structure of the geometric measurement apparatus 10 with the structure temperature sensor 24.

The method may include measuring a thickness of a glass sheet 12 with the thickness sensor 26 and outputting a thickness of the glass sheet 12 from the thickness sensor to the process controller 28. The method may include moving the glass sheet 12 with a conveyor 14. The projecting of light from the lighting apparatus 20 may have the lighting apparatus 20 located parallel to or perpendicular to or both parallel and perpendicular to the direct of travel of the glass sheet 12. The method may include correcting the length of the glass sheet 12 for a velocity at which the conveyor 14 moves, with the process controller 28 correcting the length of the glass sheet 12 for the velocity of the conveyor 14. The projecting of light from the lighting apparatus 20 may be at a high angle of incidence to the glass sheet 12. The projecting of light from the lighting apparatus 20 may be for less than 500 milliseconds or the projection of light from the lighting apparatus 20 may be continuous. The receiving of the reflected light may be for less than 100 milliseconds.

The method may include detecting the shape of the glass sheet 12, with the shape of the glass sheet 12 being quadrilateral, elliptical, irregular, curved, quadrilateral with a quadrilateral removed, quadrilateral with an ellipse removed, elliptical with a quadrilateral removed, elliptical with an ellipse removed, irregular with a quadrilateral removed, irregular with an ellipse removed, curved with a quadrilateral removed, or curved with a quadrilateral removed. The method may include measuring defects in an edge grind quality and a beveled edge quality, with the process controller 28 determining the edge grind quality and the beveled edge quality from the size and shape of the glass sheet 12 determined by the process controller 28. The method may include stopping the conveyor 14 prior to the projecting of light from the lighting apparatus 20 onto the glass sheet 12. The method may include a pass/fail signal for accepting or rejecting 35 a glass sheet 12 based on the size and shape and/or bow intensity of the reflected fixed pattern of the glass sheet 12 output from the process controller 28. The method may include determining an inside diameter 53 and an outside diameter 55 of a glass sheet 12 from the size and shape of the glass sheet 12, with the inside diameter 53 up to a beveled edge and the outside diameter 55 up to a marginal edge 51 of the glass sheet 12, with the inside diameter 53 less than the outside diameter 55. The method may include measuring bow, or warp, in the glass sheet 12. A regular grid of lines, or fixed pattern, is projected onto the length and width of the glass sheet 12. A reflected image of the fixed pattern is captured by the camera 18. The process controller 28 may compare the reflected image of the fixed pattern with a stored image of the fixed pattern. The change in size and shape of the reflected fixed pattern image is measured and this information is used to compute the bow intensity at locations over the surface of the flat sheet 12. The method may include adjusting glass machine tools 33 with the size and shape and/or the bow intensity of the reflected fixed pattern of the glass sheet 12.

FIGS. 1A, 1B and 1C illustrate three orthogonal views of the geometric measurement apparatus 10 of the present invention. As shown in FIG. 1A, the geometric measurement apparatus 10 mainly comprises a conveyor 14 moving a glass sheet 12, a retroreflective photoeye 16 determining a position of the glass sheet 12, a sheet temperature sensor 22 for measuring the temperature of the glass sheet 12, a thickness sensor 26 for measuring the thickness of the glass sheet 12, and a lighting apparatus 20 for projecting light onto the glass sheet 12. FIG. 1B shows a side view of the geometric measurement apparatus 10 (perpendicular to the view of FIG. 1A) of the present invention with the glass sheet 12 moving from left to right and FIG. 1C shows an end view of the geometric measurement apparatus 10 (perpendicular to the views of FIGS. 1A and 1C).

Figures 2A, 2B:
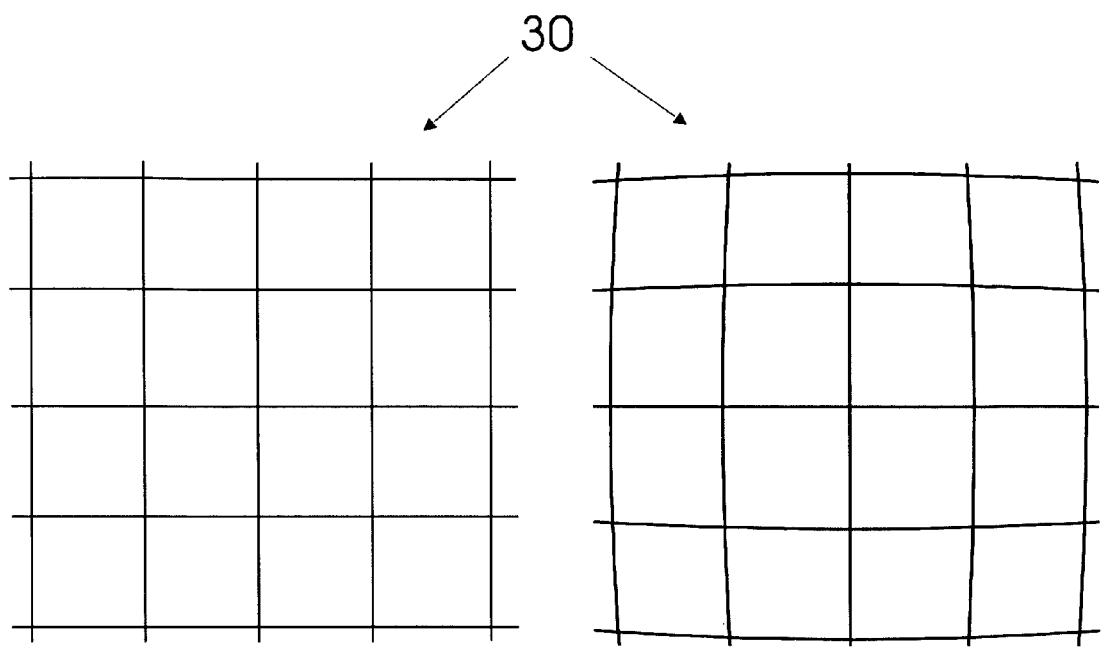
FIG. 2A of the drawings shows a top view of a calibration target as viewed from the camera in the absence of lens distortion.
FIG. 2B of the drawings shows a top view of a calibration target as viewed from the camera in the presence of lens distortion.

FIG. 2A illustrates a schematic of an image of a calibration target 30 captured by the camera 18 corrected for lens distortion. FIG. 2B illustrates a schematic of an image of a calibration target 30 captured by the camera 18 exhibiting lens distortion.

Figure 3:
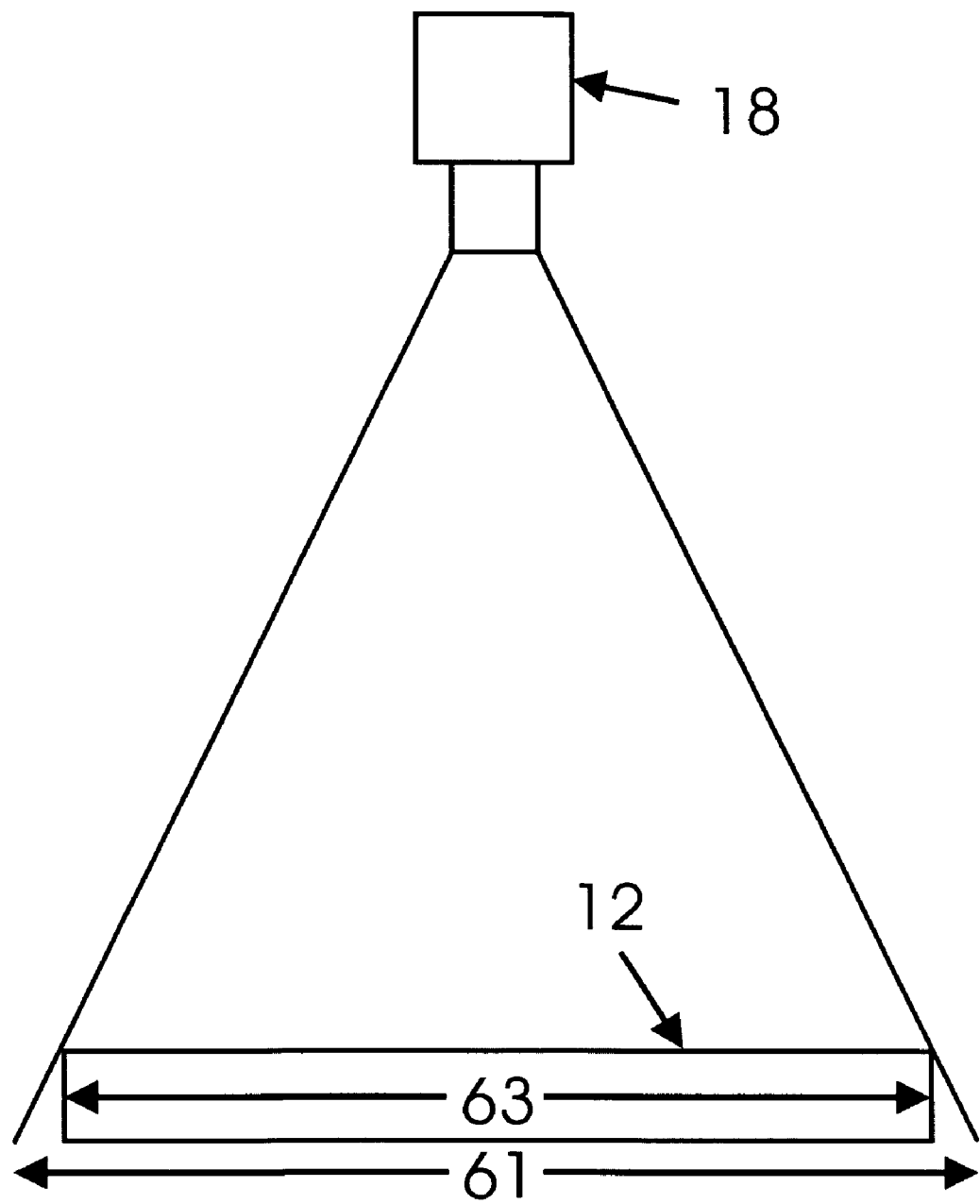
FIG. 3 of the drawings shows a side view of a glass sheet and the camera.

FIG. 3 illustrates a side schematic view of the glass sheet 12 and the camera 18 illustrating parallax observed by the camera 18. The glass sheet 12 has a thickness extending between a top side and a bottom side of the glass sheet 12. The camera 18 is not simultaneously centered on a first edge the glass sheet 12 and a second edge, opposite the first edge, of the glass sheet 12. Rays of light entering the camera 18 on the left or right side would produce an image showing an apparent measurement 61 larger than the actual size 63 of the glass sheet 12.

Figure 4:
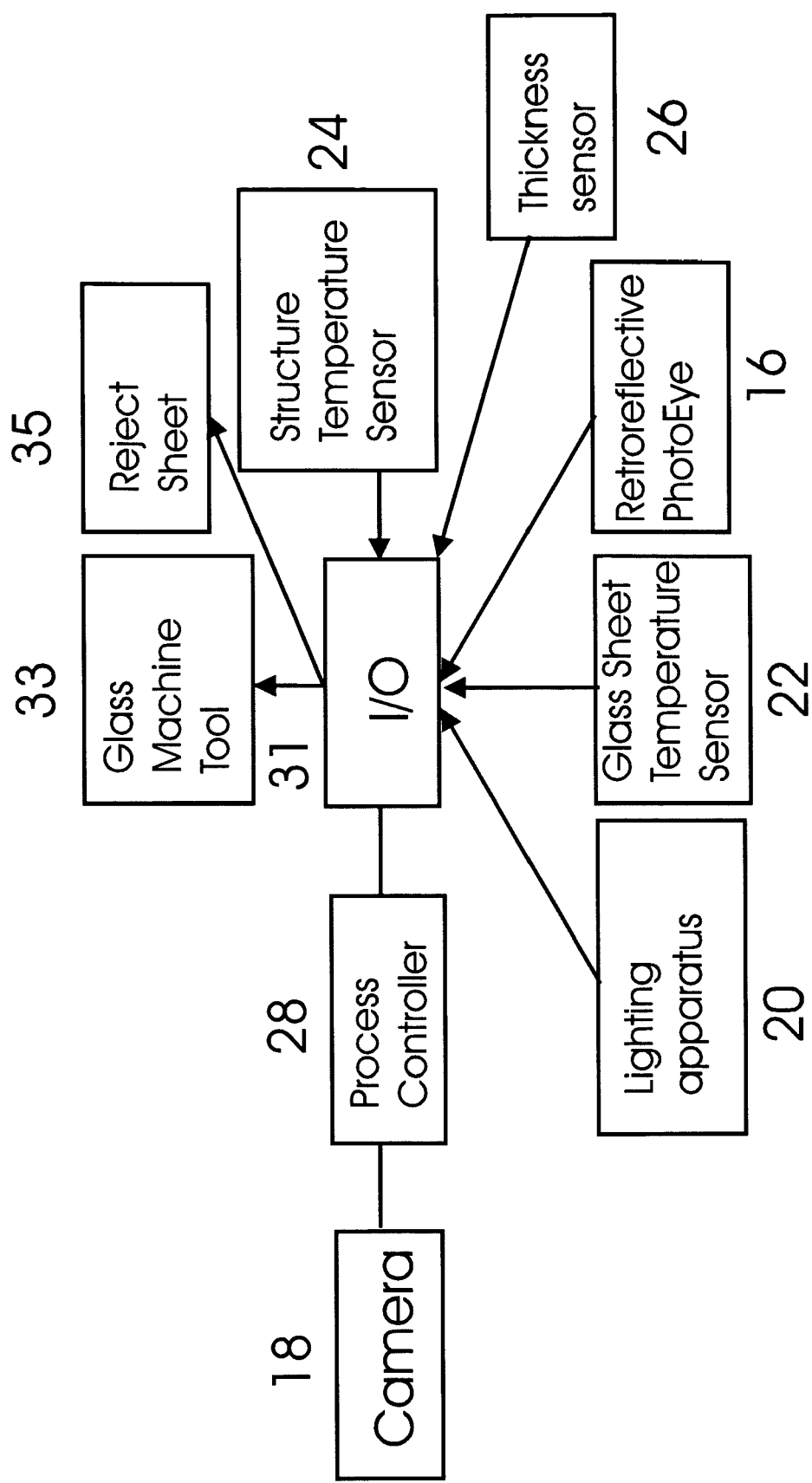
FIG. 4 of the drawings shows a process diagram of the geometric measurement apparatus.

FIG. 4 illustrates a process diagram of the geometric measurement apparatus 10. The imaging device 18 sends a signal to the process controller 28. The process controller 28 receives/sends a variety of input/out signals 31. Input signals mainly comprise the temperature of the glass sheet 12 measured by the sheet temperature sensor 22, a signal from the retroreflective photoeye 16 and the structure temperature from the structure temperature sensor 24, and the glass thickness from the thickness sensor 26. Output signals mainly comprise control of glass machine tools 33, including cutting, drilling and grinding tools and a pass/fail signal for accepting or rejecting a sheet 35.

FIG. 5 illustrates an example of a glass sheet 12 with a marginal edge 51, an inside diameter 53, an outside diameter 55, a hole 57 and a cutout 59. The geometric measurement apparatus 10 measures the size and shape of the glass sheet 12 including defects on the marginal edge 51, the hole 57 and the cutout 59 and deviations of the inside diameter 53 and the outside diameter 55 from standard values. In operation, a glass sheet passes along the conveyor 14 and past the sheet temperature sensor 22 for the glass sheet 12, the structure temperature sensor 24 and the retroreflective photoeye 16. The retroreflective photoeye 16 sends a signal to the process controller 28 when the trailing edge of the glass sheet 12 has passed the retroreflective photoeye 16. The process controller 28 then sends a signal to the camera 18 to capture an image of the glass sheet 12. The image of the glass sheet 12 is sent to the process controller 28. The sheet temperature sensor 22 sends a signal to the process controller 28 indicating the temperature of the glass sheet 12. The process controller 28 determines the size and shape of the glass sheet 12 based on the image and adjusts the size and shape of the glass sheet 12 based on the signal from the sheet temperature sensor 22. The structure temperature sensor 24 sends a signal to the process controller 28 indicating the structure temperature of the structure. The process controller 28 adjusts the size and shape of the glass sheet 12 based on the signal from the structure temperature sensor 24. The process controller 28 outputs the size and shape of the glass sheet 12 based on the image from the camera 18 and/or the values for the temperature of the glass sheet 12 from the sheet temperature sensor 22, and the structure temperature sensor 24. The thickness sensor 26 may send a signal for the thickness of the glass sheet 12 to the process controller 28 which the process controller 28 uses to adjust the size and shape of the glass sheet 12. The conveyor 14 moves the transparent sheet 12 at a velocity and the process controller 28 corrects the size (length or width) and shape of the transparent sheet 12 for the velocity. If the size and shape of the glass sheet 12 do not match standards, the process controller 28 may send a signal to control glass machine tools 33 including cutting, drilling or grinding tools or a pass/fail signal to accept or reject the sheet 35.

FIGS. 6A, 6B and 6C illustrate cross sectional stylized views of several of many possible configurations of a glass sheet 12 deformed by roll or bow.

FIGS. 7A, 7B and 7C illustrate reflected images of a projected fixed pattern corresponding, respectively to FIGS. 6A, 6B and 6C. The convexity in the glass sheet 12 shown in FIG. 6A, results in individual vertical lines in the reflected fixed pattern being closer together than in the projected fixed pattern, as shown in FIG. 7A. The concavity in the glass sheet 12 shown in FIG. 6B, results in individual vertical lines in the reflected fixed pattern being further apart than in the projected fixed pattern, as shown in FIG. 7B. The convexity on the left side and the concavity on the right side in the glass sheet 12 shown in FIG. 6C, results in individual vertical lines in the reflected fixed pattern being closer together on the left side and farther apart on the right side compared with the projected fixed pattern as shown in FIG. 7C.

The foregoing discussion discloses and describes merely exemplary embodiments of the present invention. Upon review of the specification, one skilled in the art will readily recognize from such discussion, and from the accompanying drawings and claims, that various changes, modifications and variations can be made therein without departing from the spirit and scope of the invention as defined in the following claims.

What is claimed is:

1. An apparatus which measures a size, a marginal edge and a two-dimensional shape of a transparent sheet comprising:
    a lighting apparatus projecting light at the transparent sheet;
    an imaging device receiving the light from the transparent sheet, and;
    a process controller, with the imaging device outputting an image of said transparent sheet to the process controller and with the process controller outputting the size, the marginal edge and the two-dimensional shape of the transparent sheet from said image.

2. The apparatus of claim 1 wherein the size and shape output from the process controller is a pass/fail signal.

3. The apparatus of claim 1 further comprising a sheet temperature sensor and/or a structure temperature sensor, with the sheet temperature sensor outputting a sheet temperature to the process controller and/or with the structure temperature sensor outputting a structure temperature to the process controller, and with the process controller using the sheet temperature and/or the structure temperature to correct the size and the shape of the transparent sheet due to thermal expansion or contraction.

4. The apparatus according to claim 1 wherein a calibration target is used to calibrate the apparatus, with the calibration target having a two-dimensional pattern.

5. The apparatus of claim 1 wherein a thickness sensor measures a thickness of the transparent sheet, with the thickness sensor outputting a thickness of the transparent sheet to the process controller.

6. The apparatus of claim 1 further comprising a conveyor moving the transparent sheet.

7. The apparatus of claim 6 wherein the conveyor moves the transparent sheet at a velocity and the process controller corrects the size and the shape of the transparent sheet for the velocity.

8. The apparatus of claim 1 wherein the lighting apparatus is directed at a high angle of incidence to the transparent sheet.

9. The apparatus of claim 1 wherein the output from the process controller of the shape of the transparent sheet is quadrilateral, elliptical, irregular, curved, quadrilateral with a quadrilateral removed, quadrilateral with an ellipse removed, elliptical with a quadrilateral removed, elliptical with an ellipse removed, irregular with a quadrilateral removed, irregular with an ellipse removed, curved with a quadrilateral removed, or curved with a quadrilateral removed.

10. The apparatus of claim 1 wherein the size and the shape of the transparent sheet is used to adjust glass machine tools.

11. The apparatus of claim 1 wherein the transparent sheet has an inside diameter up to a beveled edge and an outside diameter up to an edge of the transparent sheet, with the inside diameter smaller than the outside diameter, and with the inside diameter and the outside diameter determined from the size and shape of the transparent sheet output from the process controller.

12. The apparatus of claim 1 wherein a fixed pattern is projected onto the transparent sheet, with a reflected image of the fixed pattern measured for changes in the size and the shape of the transparent sheet, with the changes used to compute bow intensity.

13. A method of measuring a size, a marginal edge and a two-dimensional shape of a transparent sheet comprising:
   projecting light at the transparent sheet from a lighting apparatus;
   receiving the light from the transparent sheet with an imaging device;
   outputting an image of said transparent sheet from the imaging device to a process controller, and;
   outputting from said process controller the size, the marginal edge and the two-dimensional shape of the transparent sheet from said image.

14. The method of claim 13 wherein outputting the size and shape of the transparent sheet is a pass/fail signal.

15. The method of claim 13 further comprising measuring a sheet temperature of the transparent sheet with a sheet temperature sensor and/or measuring a structure temperature with a structure temperature sensor, outputting the glass sheet temperature from the sheet temperature sensor to the process controller and/or outputting the structure temperature from the structure temperature sensor to the process controller, using the sheet temperature and/or the structure temperature in the process controller to adjust the size and the shape of the transparent sheet.

16. The method of claim 13 further comprising calibrating the apparatus using a calibration target, wherein the calibration target has a two-dimensional pattern.

17. The method of claim 13 further comprising measuring a thickness of the transparent sheet with a thickness sensor and outputting the thickness of the transparent sheet from the thickness sensor to the process controller.

18. The method of claim 13 further comprising moving the transparent sheet with a conveyor.

19. The method of claim 18 further comprising correcting the length of the transparent sheet, with the moving the transparent sheet being at a velocity, and with the process controller correcting the length of the transparent sheet with the velocity.

20. The method of claim 13 wherein projecting light is at a high angle of incidence to the transparent sheet.

21. The method of claim 13 further comprising detecting the shape of the transparent sheet, with the shape of the transparent sheet being quadrilateral, elliptical, irregular, curved, quadrilateral with a quadrilateral removed, quadrilateral with an ellipse removed, elliptical with a quadrilateral removed, elliptical with an ellipse removed, irregular with a quadrilateral removed, irregular with an ellipse removed, curved with a quadrilateral removed, or curved with a quadrilateral removed.

22. The method of claim 13 further comprising adjusting glass machine tools with the size and shape of the transparent sheet.

23. The method of claim 13 further comprising determining an inside diameter and an outside diameter of a transparent sheet from the size and size of the transparent sheet, with inside diameter up to a beveled edge and the outside diameter up to an edge of the transparent sheet with the inside diameter less than the outside diameter.

24. The method of claim 13 further comprising projecting a fixed pattern onto the transparent sheet, measuring a reflected image of the fixed pattern for changes in the size and the shape of the transparent sheet, and computing bow intensity from the changes in the size and the shape.

* * * * *